US012341851B2

(12) United States Patent
Saxon et al.

(10) Patent No.: US 12,341,851 B2
(45) Date of Patent: Jun. 24, 2025

(54) SYSTEMS, METHODS, AND SOFTWARE FOR ACCESSING AND DISPLAYING DATA FROM IMPLANTED MEDICAL DEVICES

(71) Applicant: UNIVERSITY OF SOUTHERN CALIFORNIA, Los Angeles, CA (US)

(72) Inventors: Leslie A. Saxon, Los Angeles, CA (US); Steve McLelland, Los Angeles, CA (US); Brittain Bush, Los Angeles, CA (US); Mona Sobhani, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 520 days.

(21) Appl. No.: 17/315,797

(22) Filed: May 10, 2021

(65) Prior Publication Data

US 2021/0350919 A1    Nov. 11, 2021

Related U.S. Application Data

(60) Provisional application No. 63/021,918, filed on May 8, 2020.

(51) Int. Cl.
| | | |
|---|---|---|
| *H04L 67/125* | (2022.01) | |
| *G06F 16/78* | (2019.01) | |
| *G16H 10/60* | (2018.01) | |
| *G16H 40/63* | (2018.01) | |
| *G16H 50/20* | (2018.01) | |

(52) U.S. Cl.
CPC ........ *H04L 67/125* (2013.01); *G06F 16/7867* (2019.01); *G16H 10/60* (2018.01); *G16H 40/63* (2018.01); *G16H 50/20* (2018.01)

(58) Field of Classification Search
None
See application file for complete search history.

(56) References Cited

U.S. PATENT DOCUMENTS

| | | | | |
|---|---|---|---|---|
| 2006/0122863 A1* | 6/2006 | Gottesman | ............. | G16H 10/60 705/2 |
| 2011/0245633 A1* | 10/2011 | Goldberg | ............... | A61B 5/165 600/323 |
| 2012/0059954 A1* | 3/2012 | Gilson | ................. | G11B 27/005 709/246 |
| 2012/0277543 A1* | 11/2012 | Homchowdhury | .... | A61B 5/002 600/300 |
| 2018/0060520 A1* | 3/2018 | Degen | ................... | G16H 80/00 |

* cited by examiner

*Primary Examiner* — Stella Higgs
(74) *Attorney, Agent, or Firm* — Foley & Lardner LLP

(57) ABSTRACT

Systems, methods, and software for accessing, processing and displaying data related to an implanted medical device. A system may include at least one server. The at least one server may be configured to receive raw data from the implanted medical device. The at least one server may be further configured to translate the raw data to readable data by machine learning algorithms trained under supervision of one or more medical professionals. The at least one server may be further configured to transmit the readable data to a computing device configured to display the readable data to a user.

19 Claims, 15 Drawing Sheets

SYSTEMS, METHODS, AND SOFTWARE FOR ACCESSING AND DISPLAYING DATA FROM IMPLANTED MEDICAL DEVICES

CROSS REFERENCE TO RELATED APPLICATIONS

This application claims priority to and the benefit of U.S. Provisional Patent Application No. 63/021,918, titled "System and Method for Accessing and Displaying Implanted Heart Device Data" and filed on May 8, 2020, the entire contents of which is herein incorporated by reference in its entirety.

BACKGROUND

1. Field

The present disclosure relates to medical implants and medical implants data, and more particularly, to systems, methods, and software for accessing, processing and displaying data related to a medical device (e.g., an implanted heart device) implanted in the human body.

2. Description of the Related Art

Many current medical implants, such as implantable heart devices (e.g., defibrillators, pacemakers, etc.), are outdated and/or are not state of art to meet today's medical needs. The data from these devices are generally pulled into a backend server without user transparency. For example, a Boston Scientific® legacy pacemaker may collect data and transmit the data to Boston Scientific's backend server that compiles the data into a summarized PDF report. Similarly, the physician might have to login to the Abbott® database to view their patients' data, including the report, who were implanted with Abbott® devices. Likewise, the physician may have to access the Medtronic® database to access remotely collected data from Medtronic® devices. Thus, currently, a centralized database for a physician to view all backend data from all patients does not exist. Furthermore, the patient may never see this data and thus may not be informed about how their device is working or important aspects of their health. Many patients should have access to this data to better monitor and maintain their health. Due to many factors, physicians aren't always able to spend time educating their patients on a regular basis. Therefore, there is a need for improved transparency in access to patient data from a device implanted in the human body.

SUMMARY

Described herein are systems, methods, and software for accessing, processing and displaying data received from an implanted medical device, such as implanted heart device data, on a remote mobile device. As an example, the data may be received from the implanted heart device. Heart-related information may be processed and then displayed on the remote mobile device based on the data received from the implanted heart device. Alerts may also be displayed on the remote mobile device based on the data received from the implanted heart device. Respective videos associated with the alerts may also be displayed.

A system for accessing, processing and displaying data related to an implanted medical device (e.g., an implanted heart device) may include at least one server. The at least one server may be configured to receive raw data from the implanted medical device. The at least one server may be further configured to process (e.g., translate) the raw data to readable data by machine learning algorithms trained under the supervision of one or more medical professionals. The at least one server may be further configured to transmit the readable data to a computing device configured to display the readable data to a user. The readable data from an implanted heart device may include at least one of heart pacing and/or beats per minute. The at least one server may be further configured to receive device alerts from the implanted medical device and process, filter, and translate the device alerts by the machine learning algorithms and transmit the processed, filtered, and translated device alerts to the computing device. The at least one server may be further configured to recommend videos associated with the device alerts by the machine learning algorithms and transmit the recommended videos to the computing device in conjunction with the device alerts. The at least one server may be further configured to host a social network including the user and at least one caregiver of the user.

The computing device may be at least one of a smartphone, a tablet computer, a laptop, or a wearable mobile device. The computing device may be capable of communicating with any implanted medical device without regard to a manufacturer of the implanted medical device. The computing device may include a user interface including a dashboard section having a heart icon corresponding to the heart-related information, an activity icon corresponding to activity-related information, and a battery icon corresponding to battery-related information of the implantable heart device. The user interface may further include an alert section having the displayed alerts and icons corresponding to the respective videos associated with the alerts. The computing device may sound an alarm or may cause a vibration to the user to inform the user that a new alert has been received.

A method for accessing, processing and displaying data related to an implanted medical device may include receiving, by a computing device, data from the implanted medical device. The method may further include displaying, by the computing device, heart-related information based on the data received from the implanted medical device. The method may further include displaying, by the computing device, alerts based on the data received from the implanted medical device. The method may further include displaying, by the computing device, respective videos associated with the alerts. The method may further include receiving, by the computing device, activity data from an activity-tracking device and displaying, by the computing device, activity-related information based on the activity data. The method may further include displaying, by the computing device, battery information of the implanted medical device based on the data received from the implanted medical device.

A non-transitory computer readable memory may store program instructions. The program instructions may include program instructions to configure at least one processor to receive data from an implanted medical device by a wireless transceiver. The wireless transceiver may be capable of communicating with any implanted medical device without regard to a manufacturer of the implanted medical device. The program instructions may further include program instructions to configure at least one processor to display heart-related information based on the data received from the implanted medical device on a display of a mobile device. The program instructions may further include program instructions to configure at least one processor to display alerts based on the data received from the implanted medical device on the display of the mobile device. The program instructions may further include program instructions to configure at least one processor to display respective videos associated with the alerts on the display of the mobile device. The program instructions may further include program instructions to configure at least one processor to receive activity data from an activity-tracking device and display activity-related information based on the activity data on the display of the mobile device. The program instructions may further include program instructions to configure at least one processor to display battery information of the implanted medical device based on the data received from the implanted medical device on the display of the mobile device.

The program instructions may further include program instructions to configure at least one processor to generate one or more graphs based on the data received from the implanted medical device and display the one or more graphs on the display of the mobile device. The one or more graphs may include a graph of heart beats per minute received from the implanted medical device over a first predetermined time period or a graph of activity over a second predetermined time period or a graph of ventricular pacing and atrial pacing over a third predetermined time period.

The program instructions may further include program instructions to configure at least one processor to display a user interface including a dashboard section having a heart icon corresponding to the heart-related information, an activity icon corresponding to activity-related information, and a battery icon corresponding to battery-related information of the implanted medical device on the display of the mobile device. The user interface may further include an alert section having the displayed alerts and icons corresponding to the respective videos associated with the alerts.

BRIEF DESCRIPTION OF THE DRAWINGS

Other systems, methods, features, and advantages of the present invention will be or will become apparent to one of ordinary skill in the art upon examination of the following figures and detailed description. It is intended that all such additional systems, methods, features, and advantages be included within this description, be within the scope of the present invention, and be protected by the accompanying claims. Component parts shown in the drawings are not necessarily to scale and may be exaggerated to better illustrate the important features of the present invention. In the drawings, like reference numerals designate like parts throughout the different views, wherein:

DETAILED DESCRIPTION OF THE DRAWINGS

Figure 1:
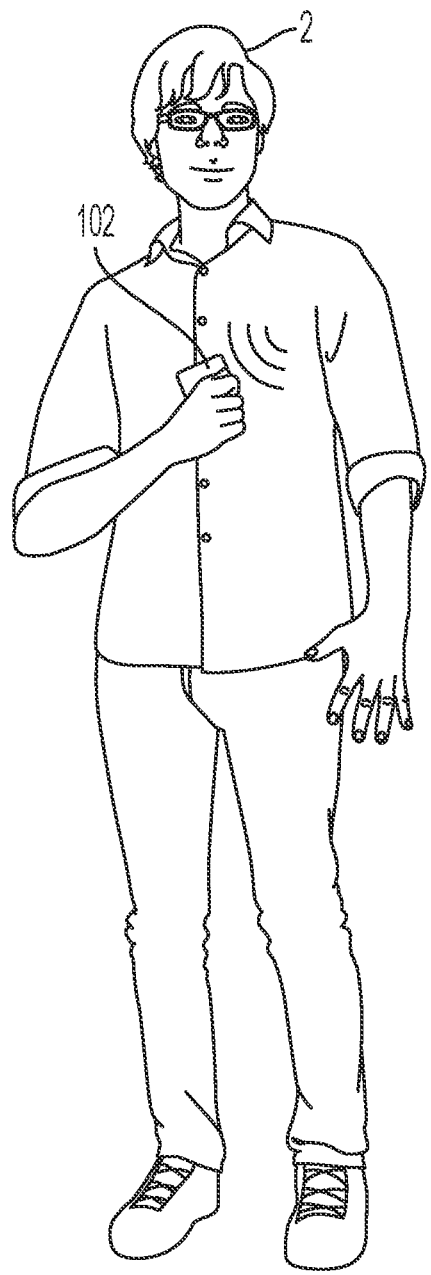
FIG. 1 illustrates a patient using a mobile device of a system capable of accessing, processing and displaying data of an implanted medical device of the patient according to an aspect of the present disclosure.

The systems, methods, and software described herein are used for accessing, processing and displaying data related to an implanted medical device, for example, an implanted heart device. The implanted medical device can be any medical device implanted into the body of a human. For illustrative purposes, the implanted medical device is an implanted heart device.

The software may be a mobile application for Cardiac Rhythm Management (CRM) patients or users to help drive their own disease or health management as well as caregivers to help patients with their disease or health management. The mobile application may be run on a mobile device, such as a smartphone, a tablet, a smartwatch, a laptop, or any other device with computing capabilities. With the mobile application, patients may be advantageously given access to all of their relevant health information in real-time from their CRM devices, such as their heart rate, pacing, activity, and device battery life. Caregivers may also be given access to all or some of their patients' relevant health information from their patients' CRM devices to help their patients with health monitoring, management and care. The mobile application includes and runs software that is used to receive, process, filter, and/or track the data received from the implanted medical device and display the patient data on a screen or display of the mobile device.

The mobile application may obtain data related to an implanted medical device in several ways. In some embodiments, the mobile application may obtain the data from a remote server. The mobile application may present user authentication credentials to obtain the data from the remote server. The remote server may be managed by a manufacturer of the implanted medical device and/or an implanting center where the implanted medical device was implanted in the patient. The mobile application may automatically receive the data from the remote server periodically (e.g., daily, every other day, every hour, when new information is available, when urgent information is needed to be sent to and received by the patient and/or the caregiver in real-time, etc.). In some embodiments, the mobile application may retrieve the data when prompted by the user.

The mobile application may connect directly to the implanted medical device via Bluetooth or any other data communications protocol. The mobile application may be device/company agnostic, which may allow the mobile application to pull data from any implanted medical device. The mobile application may also connect to other devices, such as wearables like the Apple® Watch or FitBit® to track activity.

The mobile application may provide a dashboard with health information (e.g., pacing, bpm, etc.), activity information (e.g., tracking the user's exercise, steps per day, etc.), battery information (e.g., battery condition, state of charge, life of battery, percentage charge remaining, etc.) of the implantable device, and/or any device alerts (e.g., "Atrial fibrillation was detected"). In some embodiments, the device alerts may link to further educational information, such as a video explaining what the detected event is and further steps to take by the patient or the user.

The mobile application may also provide an education portal with a library of short, informative videos from a physician explaining things such as "What is atrial fibrillation?", "Why you received this alert?", etc. The alerts are specific and targeted to the needs of the patient or the user and may be based on the current state of health of the patient. The mobile application may also provide a profile screen with basic information of the user (e.g., the patient), such as the doctor identification of the patient, device serial number, etc.

FIG. 1 illustrates a patient 2 using a mobile device 102 of a system 4 (see FIG. 4) capable of accessing, processing and displaying data of an implanted heart device 6 (see FIG. 2) of the patient 2. The term "patient" may be interchangeable with "user." In some embodiments, the mobile device 102 may be a tablet, a smartwatch, a laptop, or any other device with computing capabilities. A smartphone is shown in FIG. 1 as an example of a mobile device 102. In some embodiments, the mobile device 102 may communicate directly with the implanted heart device 6. In some embodiments, the mobile device 102 may communicate with a server or servers in communication with the implanted heart device 6.

Figure 2:
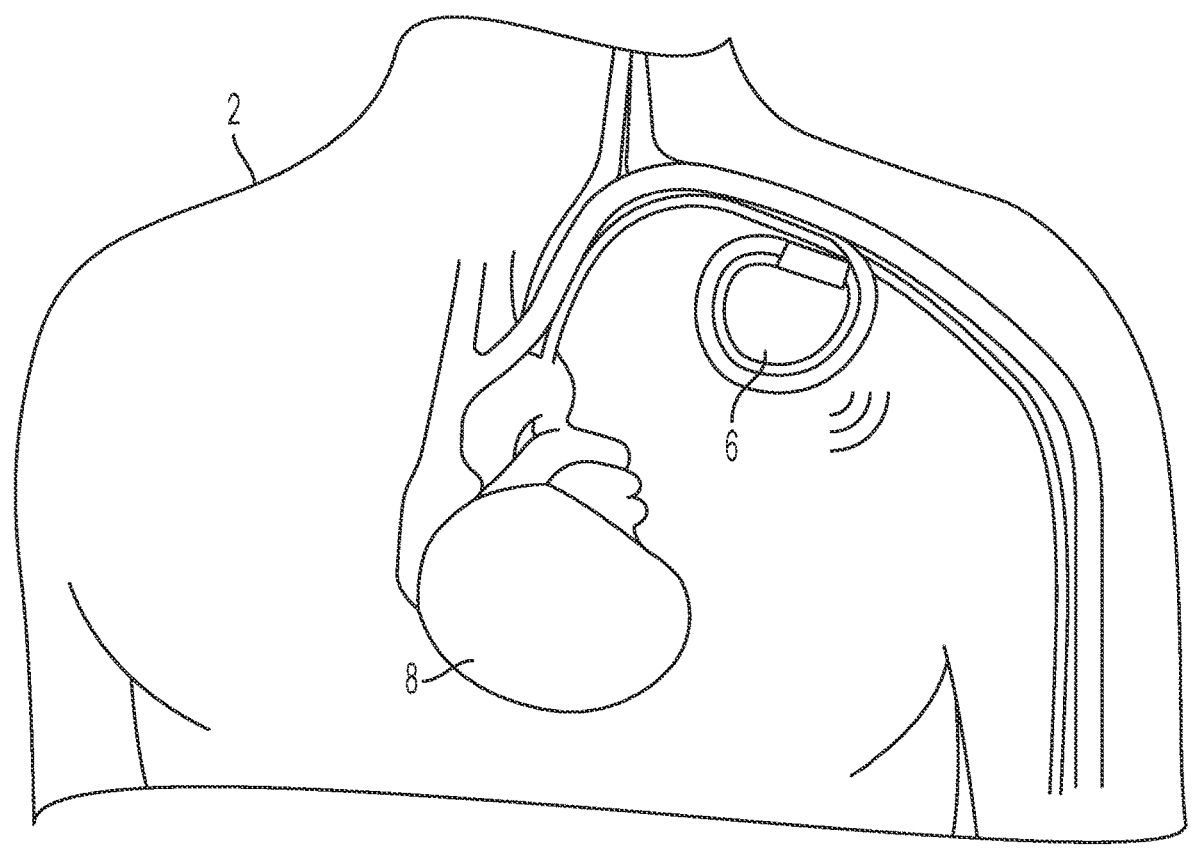
FIG. 2 illustrates an implanted heart device of the patient of FIG. 1 according to an aspect of the present disclosure.

FIG. 2 illustrates the implanted heart device 6. The implanted heart device 6 may be a defibrillator attached to a heart 8 of the patient 2 as shown in FIG. 2. The defibrillator may be with or without synchronization. In some embodiments, the implanted heart device 6 may be a pacemaker. In some embodiments, the implanted heart device 6 may be replaced with cardiac and vascular devices such as an implantable loop recorder or pulmonary artery sensors. In some embodiments, the implanted heart device 6 may be replaced with other implanted devices such as a left ventricular assist device, a mechanical heart valve or clip, a left atrial occlusive device, or an intra atrial shunt. In some embodiments, the implanted heart device 6 may be replaced with a non-cardiac device, such as joint prosthetics.

The implanted heart device 6 may communicate with the mobile device 102 via Bluetooth or any other data communications protocol. The mobile device 102 may communicate with the implanted heart device 6 irrespective of the manufacturer or model of the implanted heart device 6. The implanted heart device 6 may communicate with servers via an Internet connection established via WiFi.

Figure 3:
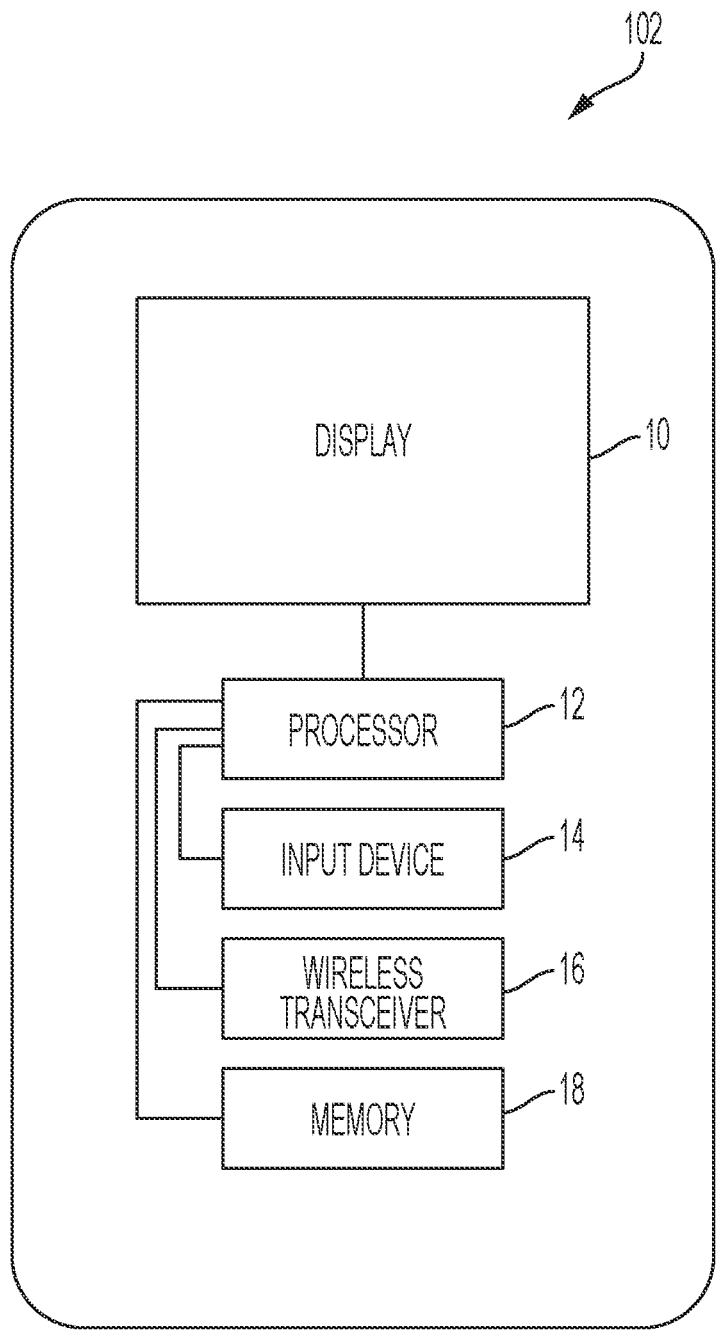
FIG. 3 illustrates a block diagram showing various components of the mobile device of FIG. 1 according to an aspect of the present disclosure.

FIG. 3 illustrates a block diagram showing various components of the mobile device 102. The mobile device 102 may have a display 10, a processor 12, an input device 14, a wireless transceiver 16, and a memory 18.

The display 10 may be a liquid crystal display (LCD), a light-emitting diode display (LED), an organic light emitting diode (OLED), a plasma display, a cathode-ray tube (CRT) display, a digital light processing display (DLPT), a microdisplay, a projection display, or any other display appreciated by one of ordinary skill in the art. The display 10 may display user interfaces, texts, images, and/or the like. The interface may allow a user to control the mobile device 102 and one or more components of the system 4 (see FIG. 4). The interface may further allow the user to view information outputted by the system 4. The display 10 may be a touchscreen and be integrated with the input device 14 to receive user input.

The processor 12 may be configured to process and execute machine-readable instructions. In some embodiments, there may be a plurality of processors 12. The processor 12 may be a microprocessor or a microcontroller by example. The processor 12 may be programmed to control the mobile application and components of the mobile device 102 based on the user's input. The display 10, the input device 14, the wireless transceiver 16, and the memory 18 may be coupled to the processor 12. The memory 18 may be used to store the software executed by the processor 12.

Input from the patient 2 (see FIG. 1) may be received via an input device 14. The input device 14 may be integrated with the mobile device 102. The input device 14 may receive visual, auditory, and/or touch inputs. For example, the input device 14 may be a camera, a microphone, a touchscreen, a button, or a remote. The input device 14 may be integrated with the display 10 of the mobile device 102. The input device 14 may receive biometric information, the user's voice, and/or the user's touch input using one or more fingers.

The wireless transceiver 16 may receive and transmit data through the Internet, WiFi, 4G, 5G, Bluetooth, Infrared, and/or the like. Some or all of the aforementioned communication methods may be available for selection by the user based on preferences or suitability (e.g., signal travel distance, signal availability, signal interference, signal travel speed, etc.).

The memory 18 may be a random-access memory (RAM), a disk, a flash memory, optical disk drives, hybrid memory, or any other storage medium that can store data. The memory 18 may store program code that are executable by the processor 12. The memory 18 may store data in an encrypted or any other suitable secure form.

Figure 4:
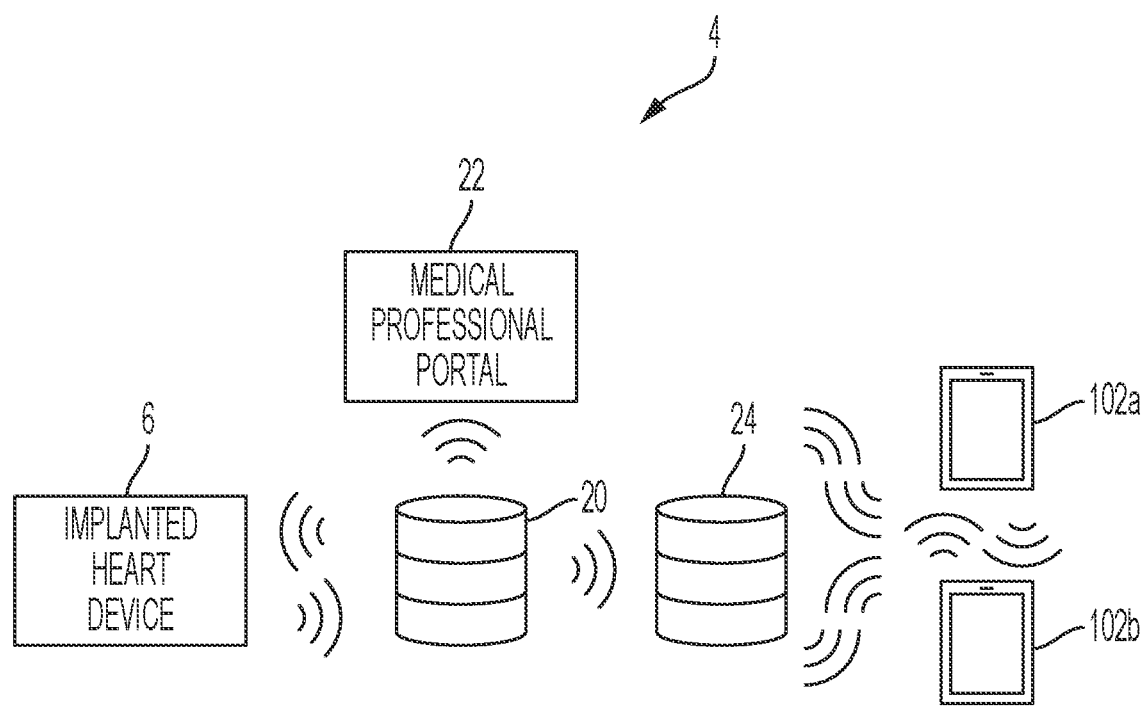
FIG. 4 illustrates a block diagram of a network of the system capable of accessing, processing and displaying data of the implanted medical device of the patient according to an aspect of the present disclosure.

FIG. 4 illustrates a block diagram of a network of the system 4 capable of accessing, processing and displaying data of the implanted heart device 6. The implanted heart device 6 may communicate with a server 20. The server 20 may be a server of the medical device manufacturer. The implanted heart device 6 may receive data from the server 20 and send raw data to the server 20 via the Internet accessed via WiFi. The raw data may include signals carrying information such as heart bpm, pacing data, and battery life of the implanted heart device 6.

The server 20 may communicate the raw data received from the implanted heart device 6 to a medical professional via a portal 22. The portal 22 may be a user interface accessible by the medical professional. The medical professional may view the raw data to be informed of the health of the patient 2 (see FIG. 1). The medical professional may also create and send a specific alert and/or message in real-time to the patient 2 via the mobile device 102.

The server 20 may convert the raw data received from the implanted heart device 6 to device alerts and biometric data. The server 20 may have a processor or processors that carry out the conversion. The server 20 may communicate the device alerts and biometric data to a server 24. The server 24 may be a server of the mobile application.

The server 24 may process and translate the biometric data for patient consumption (e.g., viewing in an understandable way) using machine learning algorithms. The machine learning algorithms may be trained under the supervision of a panel of specialized doctors (e.g., cardiology experts). For example, if the patient 2 has an association between activity and the risk for a recurrent arrhythmia based on the biometric data collected over time, the patient 2 is informed of that risk in advance. In another example, if the patient 2 has a vascular pressure sensor and a CRM device, the algorithm could be trained to identify the risk of a vascular pressure charge or the risk of an arrhythmia and inform the patient 2 proactively. The server 24 may further process, filter, and translate the device alerts for patient consumption. The biometric data and the device alerts may be interpreted and summarized in a language that is both understandable and educational to the patient as to their condition at any given moment and over time. For example, the patient 2 may be given information as to how the patient's use of certain functions of the device, like pacing support or heart failure support, relates to other aspects of the patient's clinical condition, such as drug adherence that may also be assessed by the mobile application and integrated with the device diagnostics and therapeutic information.

The server 24 may include a video content recommendation engine linked to the biometric data and device alerts. The server 24 may include a social network between the patient 2 (see FIG. 1) and the caregiver of the patient 2. The server 24 may include a content library with supported conditions and frequently asked questions.

The server 24 may simultaneously communicate with a mobile device 102a of the patient 2 (see FIG. 1) and a mobile device 102b of the caregiver. The mobile devices 102a,b may receive data from the server 24 and send data to the server 24 via the Internet accessed via WiFi. The mobile devices 102a,b may receive pacing data, heart bpm, battery life information, device alerts, and activity data from the server 24 by example. The mobile devices 102a,b may access educational videos where medical professionals explain medical concepts relevant to the medical treatment of the patient 2. The mobile devices 102a,b may further access user profiles. The user profiles may include information pertaining to the patient 2, the healthcare provider of the patient 2, serial number of the implanted heart device 6, etc.

The mobile devices 102a,b may communicate with each other. The communication may be established through the Internet, WiFi, 4G, 5G, Bluetooth, Infrared, and/or the like. For example, the mobile devices 102a,b may send messages to each other on the mobile application. The mobile device 102a of the patient 2 (see FIG. 1) may grant or revoke access to some or all of the patient data and dashboard of the mobile device 102b of the caregiver. For example, the patient 2 may only allow the caregiver to monitor the battery life of the implanted heart device 6. In another example, the caregiver may monitor all patient data and alerts received by the mobile device 102a on mobile device 102b as well as watch the informative videos available to mobile device 102a.

In some embodiments, the implanted heart device 6 may communicate directly (without the servers 20 and/or 24) with the mobile devices 102a,b. The communication may be established via Bluetooth or another communication protocol. The processor 12 may convert the raw data received from the implanted heart device 6 to device alerts and biometric data. The processor 12 may process and translate the biometric data for patient consumption using machine learning algorithms. The machine learning algorithms may be trained under the supervision of a panel of specialized doctors (e.g., cardiology experts). The processor 12 may further process, filter, and translate the device alerts for patient consumption.

Figure 5A:
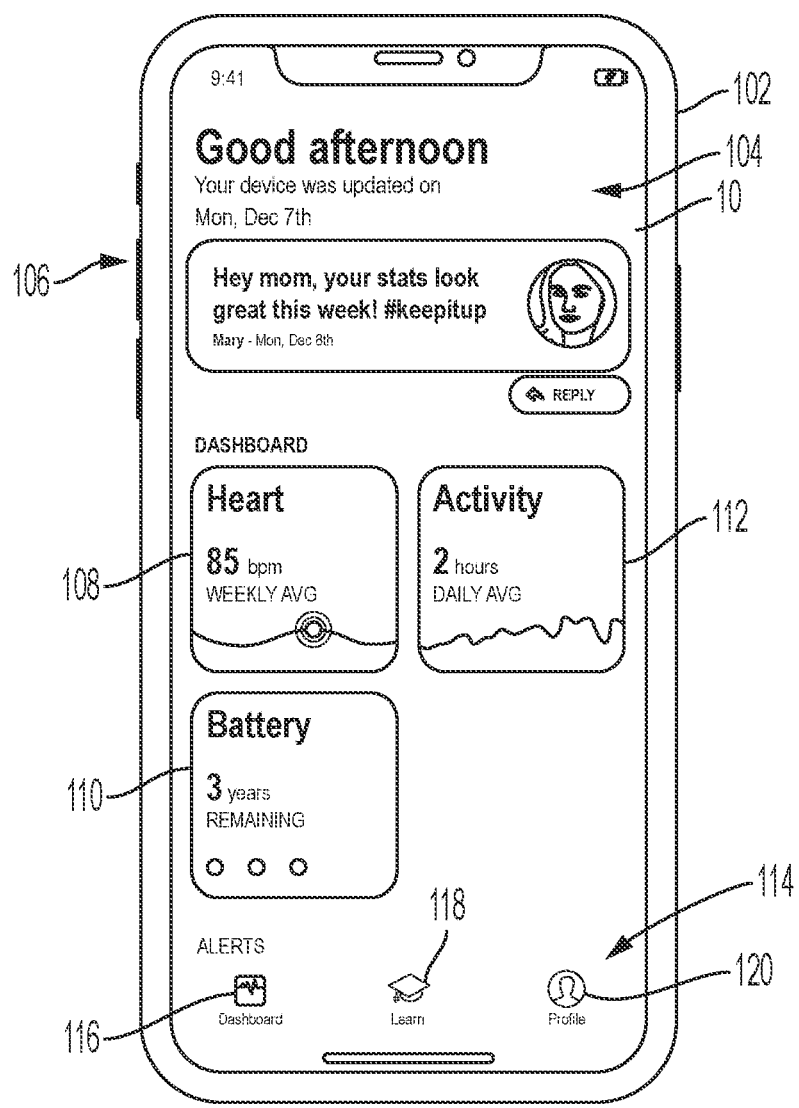
FIG. 5A illustrates a first portion of a user dashboard displayed on a display of the mobile device of FIG. 1 according to an aspect of the present disclosure.

FIG. 5A illustrates a first portion of a user dashboard displayed on the display 10 of the mobile device 102. The mobile application may be run on the mobile device 102. The user dashboard includes update information 104. The update information may provide information as to when the implanted heart device 6 (see FIG. 2) was updated. The user dashboard may also show social information 106, including messages from contacts such as a caregiver. For example, the social information 106 may be a latest message received from a child of the patient 2 (see FIG. 1) monitoring the patient data as shown in FIG. 5A.

Figure 8A:
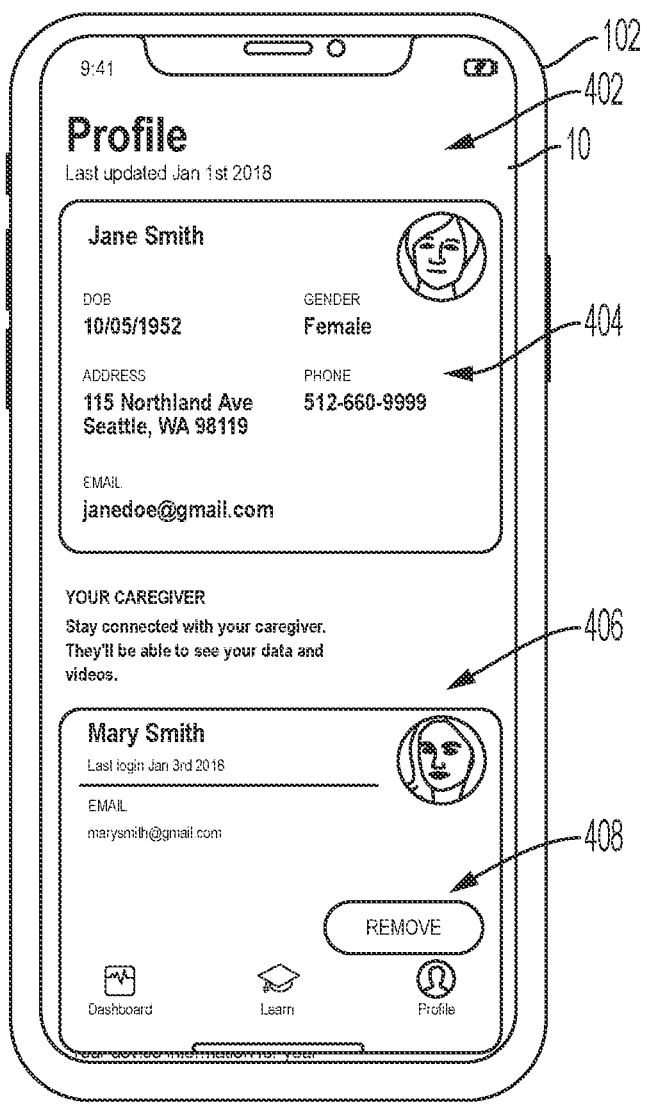
FIG. 8A illustrates a first portion of a user profile displayed on the display of the mobile device of FIG. 1 according to an aspect of the present disclosure.

The contacts (or caregivers) may be identified by the patient 2 as shown in FIG. 8A. There may be any number of caregivers associated with the patient 2. The patient 2 may authorize the addition or removal of a caregiver. The caregivers may be able to view data associated with the implanted heart device 6 (see FIG. 2) using their own respective mobile device 102b (see FIG. 4). In this way, the caregivers can be kept updated on the status of the patient 2. In some embodiments, the patient 2 may customize the data visible to each of the caregivers. The caregivers may also be able to prevent the patient 2 from restricting the data to the caregivers in situations, for example, when the patient 2 has dementia or other debilitating conditions that require or warrant the caregivers from having access to all the data for the health and safety of the patient 2.

The user dashboard may include icons 108-112. The heart icon 108 may show heart-related information (e.g., bpm and a graph) and may be selectable to display the heart screen shown in FIGS. 6A-6B. The battery icon 110 may show battery-related information and may be selectable to display additional battery-related information. The activity icon 112 may show activity-related information (e.g., hours of activity and a graph) and may be selectable to display additional activity-related information.

Figure 5B:
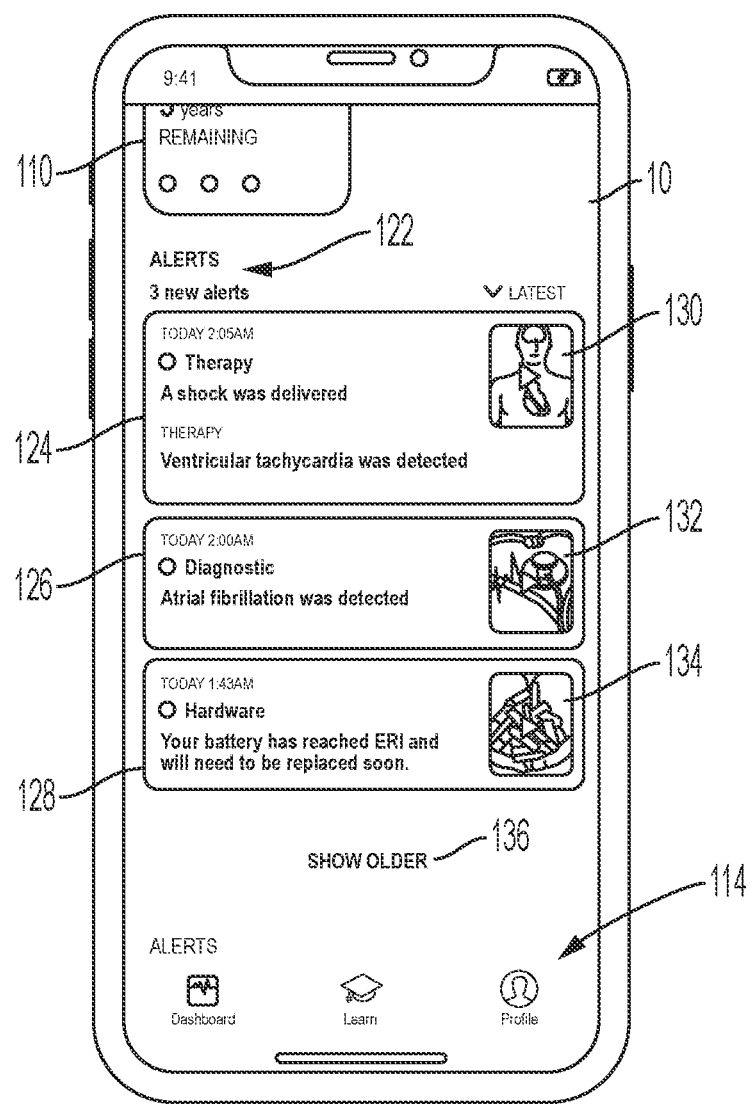
FIG. 5B illustrates a second portion of the user dashboard displayed on the display of the mobile device of FIG. 1 according to an aspect of the present disclosure.
Figure 7A:
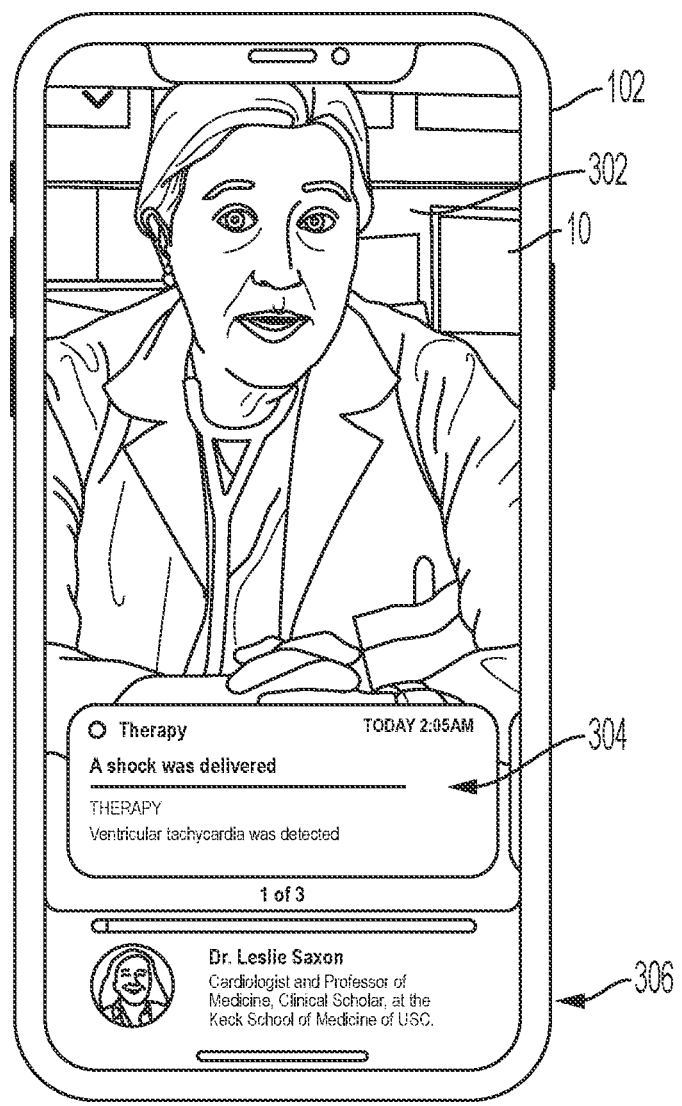
FIG. 7A illustrates a first informative video associated with a first alert being displayed on the display of the mobile device of FIG. 1 according to an aspect of the present disclosure.
Figure 7B:
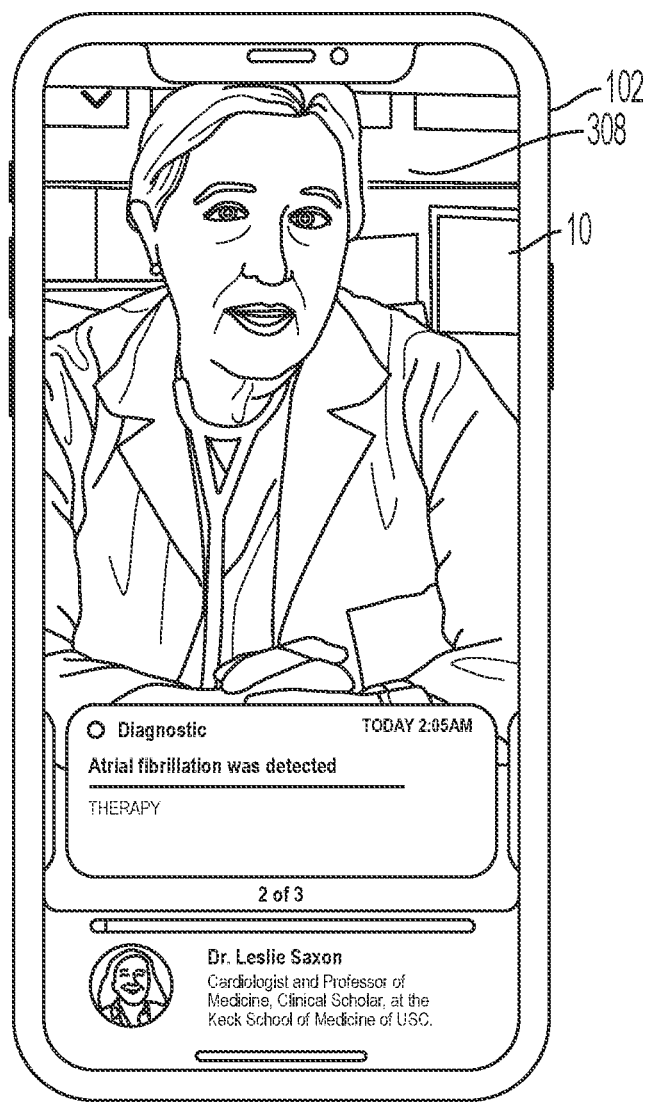
FIG. 7B illustrates a second informative video associated with a second alert being displayed on the display of the mobile device of FIG. 1 according to an aspect of the present disclosure.
Figure 8B:
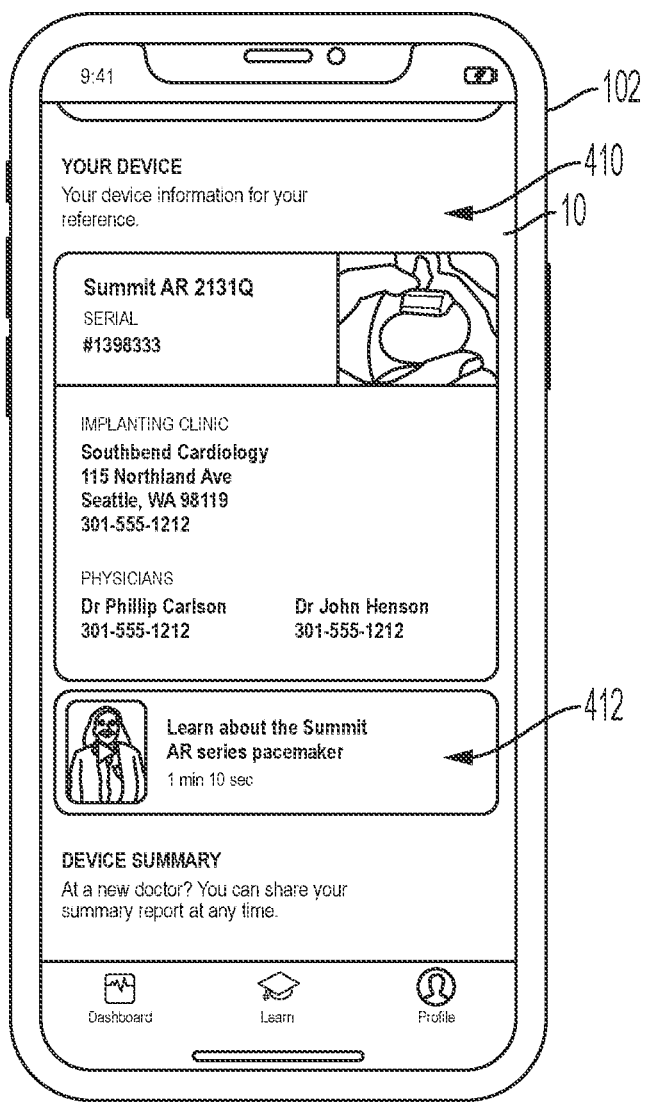
FIG. 8B illustrates a second portion of the user profile displayed on the display of the mobile device of FIG. 1 according to an aspect of the present disclosure.

A tray 114 may include icons 116-120. The dashboard icon 116 may display the dashboard, as shown in FIGS. 5A-5B. The learn icon 118 may displays videos, as shown in FIGS. 7A-7B. The profile icon 120 may display the user profile, as shown in FIGS. 8A-8B.

FIG. 5B illustrates a second portion of the user dashboard displayed on the display 10 of the mobile device 102. The second portion may be viewed when scrolled down from the first portion shown in FIG. 5A. The second portion may show an alerts section 122, with detected or scheduled alerts 124-128. Each alert 124-128 may have an accompanying video, which may be played when the respective video icons 130-134 are selected. Each of the alerts 124-128 may have a classification. For example, alert 124 may be a therapy alert, alert 126 may be a diagnostic alert, and alert 128 may be a hardware alert 128. Alert 124 may inform that a shock was delivered by the implanted heart device 6 (see FIG. 2)

as well as that a ventricular tachycardia was detected. Alert 126 may inform that atrial fibrillation was detected. Alert 128 may inform that the battery of the implanted heart device 6 has reached an elective replacement indication (ERI) period and will need to be replaced soon. Older alerts may be viewed by pressing the show older icon 136. Alerts may be sorted alphabetically or by their time of issuance, classification, or importance. The alerts may be sent to the patient 2 in real-time, right after the event has occurred. For example, alert 124 may inform the patient 2 that a shock was delivered by the implanted heart device 6. As soon as the shock is delivered to the patient 2, the implanted heart device 6 immediately (in real-time) sends a signal to the mobile device 102*a* of the patient 2 and/or the mobile device 102*b* of the caregiver to notify the patient 2 and the caregiver what just happened or occurred. Hence, the implanted heart device 6 sends a notification to the mobile devices 102*a*,*b* in real-time of any action or change in action performed by the implanted heart device 6.

Figure 6A:
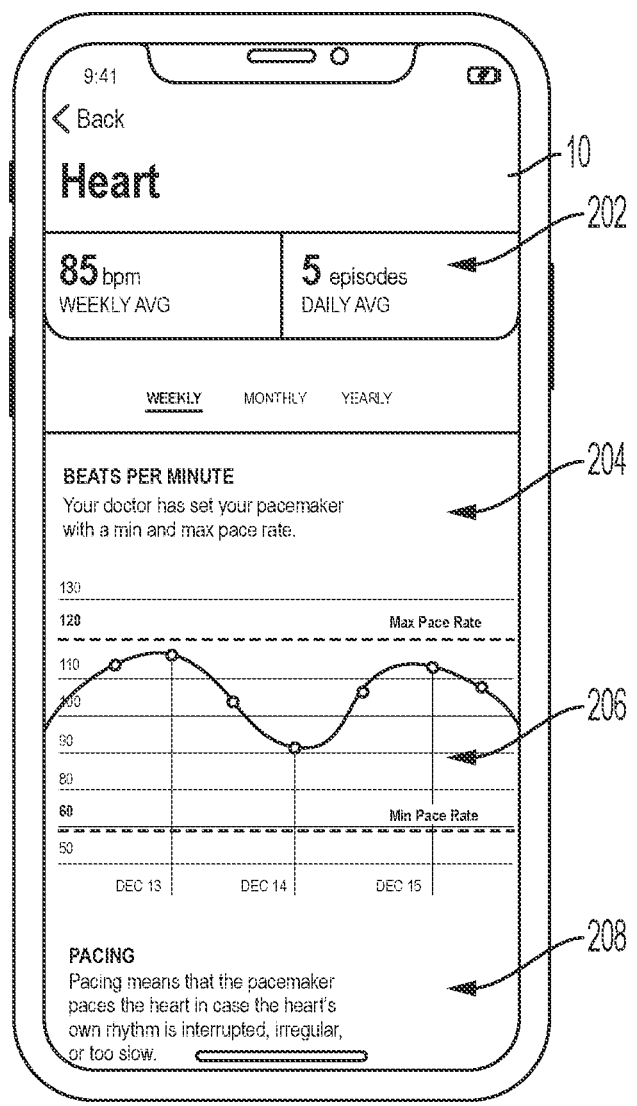
FIG. 6A illustrates a first portion of heart-related information displayed on the display of the mobile device of FIG. 1 according to an aspect of the present disclosure.

FIG. 6A illustrates a first portion of heart-related information displayed on the display 10 of the mobile device 102. The first portion may show heart-related data 202, as well as other related information 204, 208 and a graph 206. Heart-related data 202 may include heart bpm and number of episodes. The heart bpm and the number of episodes may be presented in hourly, daily, weekly, monthly, yearly averages and so on. Other related information 204 may inform the patient 2 (see FIG. 1) that the healthcare provider of the patient 2 has adjusted the settings of the implanted heart device 6 (see FIG. 2). For example, the related information 204 may show that the doctor of the patient 2 has set the implanted heart device 6 to have a minimum and a maximum pace rate as shown in FIG. 6A. Other related information 208 may provide medical information to the patient 2 about their medical treatment. For example, the medical information may be about the definition of the term "pacing" as shown in FIG. 6A. The graph 206 may be a plot of the pace rate of the patient 2. The pace rate may be plotted daily, weekly, monthly, yearly, and so on. The minimum and maximum pace rates set by the doctor of the patient 2 may be indicated on the graph 206 as shown by dashed lines in FIG. 6A.

Figure 6B:
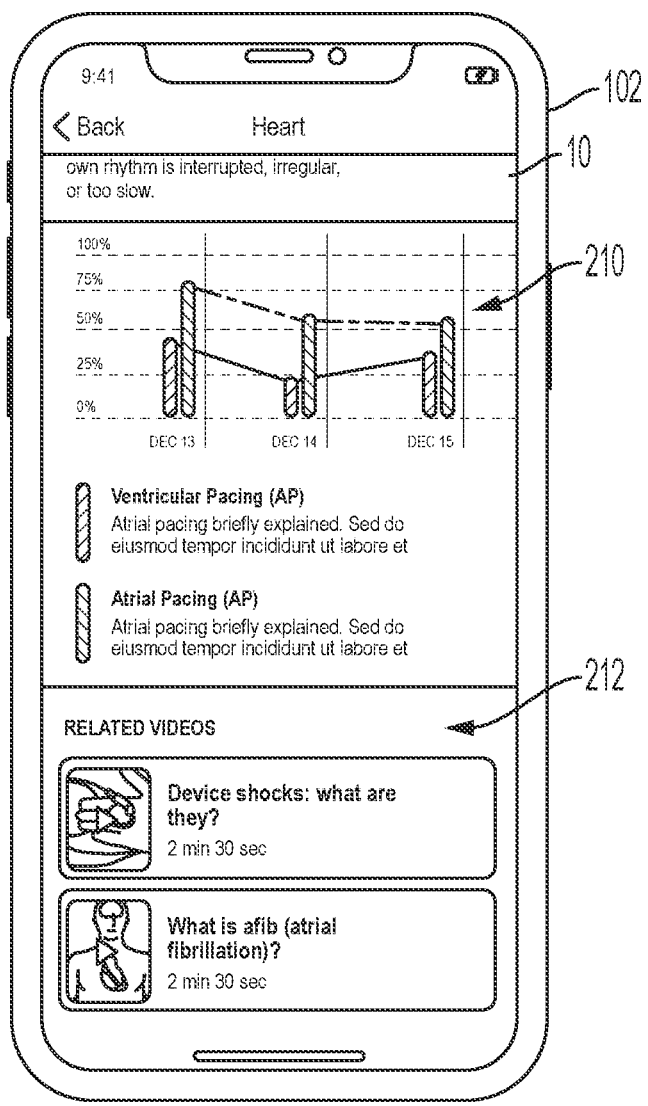
FIG. 6B illustrates a second portion of heart-related information displayed on the display of the mobile device of FIG. 1 according to an aspect of the present disclosure.

FIG. 6B illustrates a second portion of heart-related information displayed on the display 10 of the mobile device 102. FIG. 6B shows the heart-related information when scrolled downward from FIG. 6A. The second portion may show additional graphs 210 and related videos 212, which may be played when selected. The graph 210 may be a plot of ventricular pacing and atrial pacing. The plots of ventricular pacing and atrial pacing may be color coded. The ventricular pacing and atrial pacing may be measured in percentage over a time period, such as days, weeks, months, years, and so on. The second portion may further show graph related information, such as the definitions of ventricular pacing and atrial pacing.

FIG. 7A illustrates a first informative video 302 associated with the alert 124 (see FIG. 5B) being displayed on the display 10 of the mobile device 102. For example, the video 302 may be about a delivered shock and/or ventricular tachycardia that was detected as shown in FIG. 7A. The display 10 may further display a description 304 of the video or an alert and additional information 306 pertaining to the video (e.g., speaker information). The patient 2 (see FIG. 1) may scroll to other descriptions and alerts.

FIG. 7B illustrates a second informative video 308 associated with the alert 126 (see FIG. 5B) being displayed on the display 10 of the mobile device 102. For example, the video 308 may be about the atrial fibrillation that was detected as shown in FIG. 7B. The second video 308 may be played when the user swipes leftward (from the screen shown in FIG. 7A) to the next video. In some embodiments, the swiping may be towards another direction (e.g., right, up, down).

FIG. 8A illustrates a first portion of a user profile displayed on the display 10 of the mobile device 102. The first portion may include update information 402, basic patient information 404, and caregiver information 406. The update information 402 may provide information as to when the implanted heart device 6 (see FIG. 2) was updated. The basic patient information 404 may include the name, photo, date of birth, gender, address, and contact information (e.g., phone number, email) of the patient 2 (see FIG. 1) by example. The caregiver information 406 may include the name, photo, and contact information of the caregiver by example. The first portion may also include an icon 408 for removing the caregiver's association with the patient 2.

FIG. 8B illustrates a second portion of the user profile displayed on the display 10 of the mobile device 102. The second portion may be shown on the display 10 when scrolled downward from FIG. 8A. The second portion may include device information 410, including a serial number and the location where the medical device was implanted, and the associated physicians and their contact information (e.g., phone number, email). A video 412 link may also be displayed for related video content. The video 412 may provide information about the specific implanted heart device 6 (see FIG. 6).

Figure 8C:
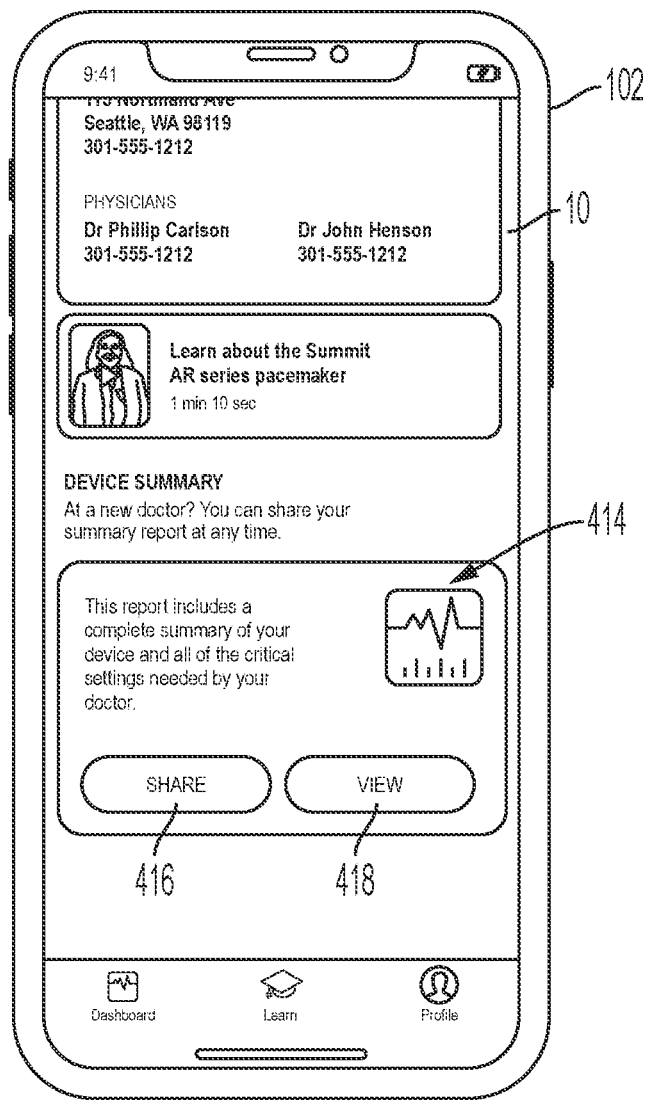
FIG. 8C illustrates a third portion of the user profile displayed on the display of the mobile device of FIG. 1 according to an aspect of the present disclosure.

FIG. 8C illustrates a third portion of the user profile displayed on the display 10 of the mobile device 102. The third portion may include report-related information 414 and a sharing icon 416 for sharing the report and a viewing icon 418 for viewing the report. The report may be shared as an attachment to a message (e.g., email, text message, social media post, etc.) and the report may be in a digital format (e.g., pdf, xlsx, png, etc.). The report may include a summary of the implanted heart device 6 (see FIG. 2) and critical settings needed by the doctor of the patient 2 (see FIG. 1).

Figure 9:
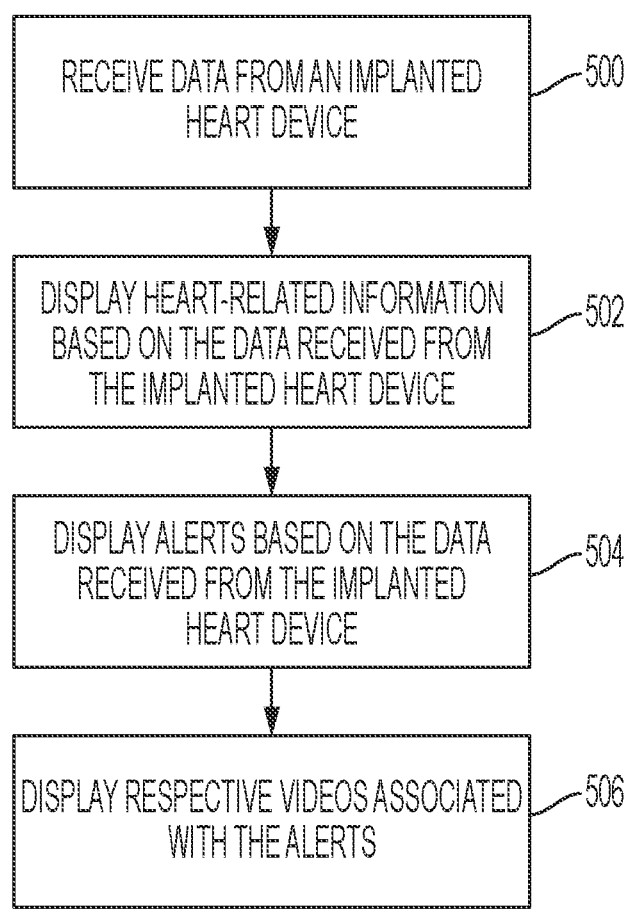
FIG. 9 illustrates a method for accessing, processing and displaying data related to the implanted medical device of the patient of FIG. 1 according to an aspect of the present disclosure.

FIG. 9 illustrates a method for accessing, processing and displaying data related to the implanted heart device 6 (see FIG. 2) of the patient 2 (see FIG. 1). The method may begin with block 500. In block 500, the method may include receiving data from the implanted heart device 6. The implanted heart device 6 may communicate with the mobile device 102 via Bluetooth or any other data communications protocol. The mobile device 102 may communicate with the implanted heart device 6 irrespective of the manufacturer or model of the implanted heart device 6. The communications protocols may be available for selection of the patient 2 based on preference or suitability (e.g., signal travel distance, signal availability, signal interference, signal travel speed, etc.). The data may include heart bpm, pacing data, and battery life of the implanted heart device 6.

In block 502, the method may include displaying heart-related information based on the data received from the implanted heart device 6. The display 10 (see FIG. 3) may perform the displaying. Heart-related information may include heart bpm and number of episodes. Heart-related information may further include medical information about heart health and heart condition treatment. Heart-related information may further include a plot of the pace rate of the patient 2. Heart-related information may further include a plot of ventricular pacing and atrial pacing.

In block 504, the method may include displaying alerts based on the data received from the implanted heart device 6. The alerts may be therapy alerts, diagnostic alerts, or hardware alerts. For example, a therapy alert may inform that a shock was delivered by the implanted heart device 6 as well as that a ventricular tachycardia was detected. In another example, a diagnostic alert may inform that atrial fibrillation was detected. In another example, a hardware alert may inform the patient 2 that the battery of the implanted heart device 6 has reached an elective replacement indication (ERI) period and will need to be replaced soon.

In block 506, the method may include displaying respective videos associated with the alerts. For example, the videos may be about a delivered shock and/or ventricular tachycardia that was detected. In another example, the video may be about the atrial fibrillation that was detected.

Figure 10:
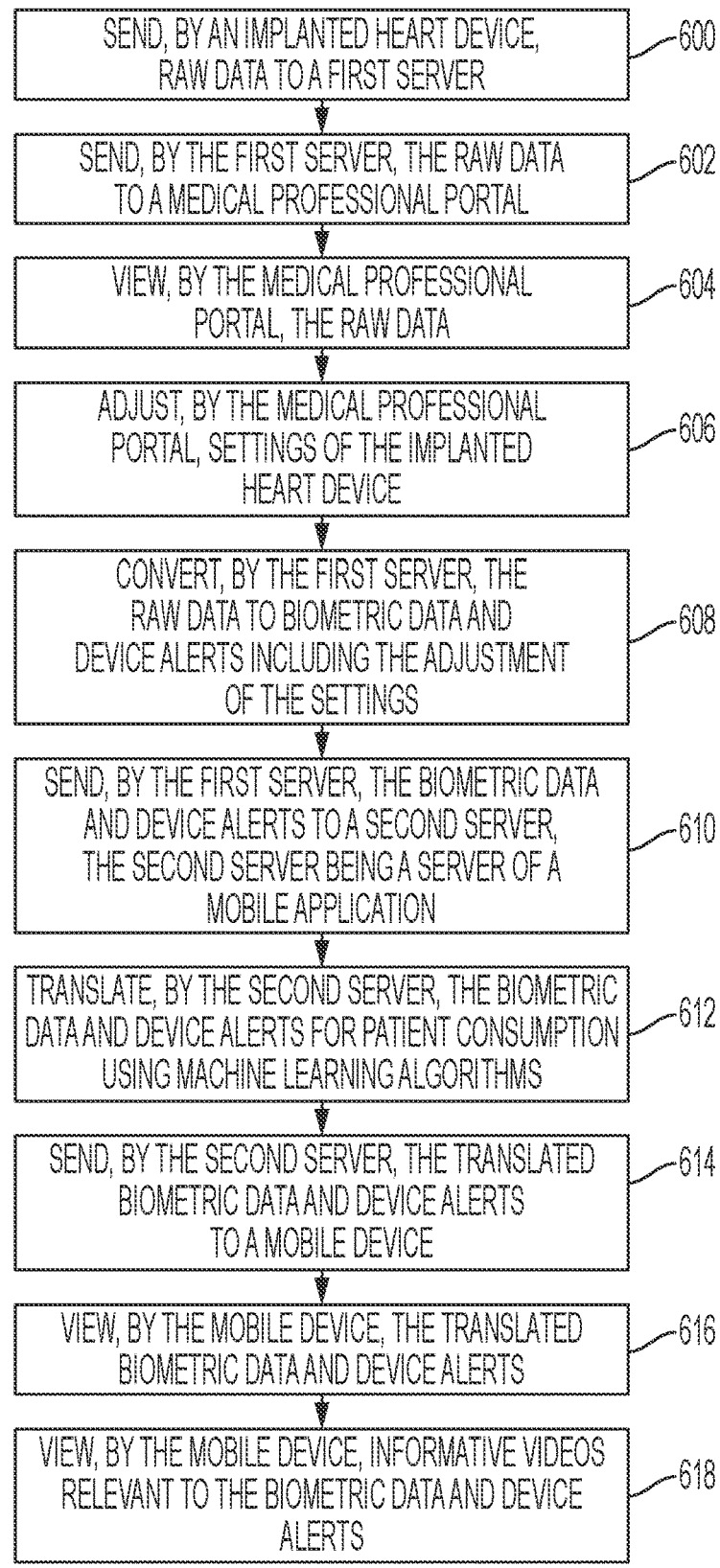
FIG. 10 illustrates a method for accessing, processing and displaying biometric data and device alerts related to the implanted medical device of the patient of FIG. 1 according to an aspect of the present disclosure.

FIG. 10 illustrates a method for accessing, processing and displaying biometric data and device alerts related to the implanted medical device. The implanted medical device may be the implanted heart device 6 (see FIG. 2) by example. The method may begin with block 600. In block 600, the method may include sending raw data to a first server 20 (see FIG. 4) by the implanted heart device 6. The raw data may include signals carrying information such as heart bpm, pacing data, and battery life of the implanted heart device 6.

In block 602, the method may include sending the raw data to a medical professional portal 22 (see FIG. 4) by the first server 20. The portal 22 may be a user interface accessible by a medical professional. In block 604, the medical professional may view the raw data to be informed of the health of the patient 2 (see FIG. 1). For example, the medical professional may view the pace rate of the patient 2 for a certain time period or an average pace rate over a certain time period.

In block 606, the method may include adjusting the settings of the implanted heart device 6 by the medical professional portal 22. For example, the medical professional may set the implanted heart device 6 to have a minimum and a maximum pace rate based on the pace rate readings viewed on the portal 22. The implanted heart device 6 may have a preset factory minimum and maximum pace rate for the patient 2 based on an average person. Through the portal 22, the medical professional may customize the pace rate range (e.g., to a patient's pace rate range) based on the patient's unique data and health conditions. When the pace rate goes above or below the adjusted range, the patient 2, the medical professional, and/or the patient's caregiver may receive an alert. In another example, the medical professional (via a mobile device, for example) may initiate a shock to the patient 2 upon analyzing the raw data to help the patient 2 achieve a normal heart rhythm. When the shock is delivered to the patient 2, the patient 2, the medical professional, and/or the patient's caregiver may receive an alert indicating that the shock has been delivered to the patient 2.

In block 608, the method may include converting the raw data to biometric data and device alerts by the first server 20. The device alerts may include one or more adjustments to the settings of the implanted heart device 6. The server 20 may have a processor or processors that carry out the conversion of the raw data to biometric data and device alerts.

In block 610, the method may include sending the biometric data and device alerts to a second server 24 (see FIG. 4) by the first server 20. The second server 24 may be a server of a mobile application. In block 612, the method may include translating the biometric data and device alerts for patient consumption using machine learning algorithms by the second server 24. The machine learning algorithms may be trained under the supervision of a panel of specialized doctors (e.g., cardiology experts). In block 614, the method may include sending the translated biometric data and device alerts to a mobile device 102 by the second server 24. The mobile devices 102$a,b$ may receive pacing data, heart bpm, battery life information, device alerts, and activity data from the server 24 by example.

In block 616, the method may include viewing the translated biometric data and device alerts by the mobile device 102. The biometric data and device alerts may be displayed on a display 10 (see FIG. 3) of the mobile device 102. In some embodiments, the translated biometric data and/or device alerts may be communicated by the mobile device 102 auditorily or via haptic feedback. For example, the patient 2 may receive an alert that the patient's pace rate is above a maximum limit set for the patient 2. The patient 2 may then take necessary steps (e.g., rest, take medication, contact doctor, etc.) to bring the patient's pace rate back to within an acceptable range.

In block 618, the method may conclude with viewing informative videos relevant to the biometric data and device alerts by the mobile device 102. The mobile device 102 may access educational videos where medical professionals explain medical concepts relevant to the medical treatment of the patient 2. The videos may be displayed on the display 10 of the mobile device 102. In some embodiments, only the audio of the video may be communicated to the patient 2.

Exemplary embodiments of the methods/systems have been disclosed in an illustrative style. Accordingly, the terminology employed throughout should be read in a non-limiting manner. Although minor modifications to the teachings herein will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

What is claimed is:

1. A system for accessing and displaying data related to a plurality of implanted medical devices of a plurality of patients, the system comprising:
a memory and one or more processors to:
receive, according to a communication protocol configured to communicate with an implanted heart device and with a mobile device, raw data in real time from the implanted medical device;
generate, based on the raw data, biometric data indicative of at least one of heart beats per minute (BPM), pacing data, ventricular tachycardia, or atrial fibrillation;
generate, in response to a shock delivered by the implanted heart device to a patient, therapy data indicating that the shock was delivered by the implanted heart device;
generate, based on the biometric data by machine learning, readable data that summarizes the biometric data in a language that is understandable to the patient; and
cause, via the communication protocol, the mobile device to present a first alert of a first classification at a first portion of a user interface, the first alert including the readable data and the biometric data; and
cause, via the communication protocol, the mobile device to present a second alert of a second classification at a second portion of the user interface, the second alert including the therapy data in response to the shock delivered by the implanted heart device to the patient and in real-time, wherein the user interface displays a list of alerts of a plurality of classifications arranged vertically on the user interface, the list of alerts comprising the first alert and the second alert, wherein the first alert comprises a first icon of a first video, and the second alert comprises a second icon of a second video;

determine that the patient selects the first icon or the second icon, and in response to determining that the patient selecting the first icon, cause, via the communication protocol, the mobile device to display the first video about the biometric data with the first alert; and in response to determining that the patient selecting the second icon, cause, via the communication protocol, the mobile device to display the second video about the delivery of the shock by the implanted heart device with the second alert.

2. The system of claim 1, the one or more processors to:
recommend one or more videos associated with the first alert; and
transmit the one or more videos to the mobile device in conjunction with the first alert.

3. The system of claim 1, the one or more processors to:
host a social network including the patient and at least one caregiver of the patient.

4. The system of claim 1, wherein the user interface including a dashboard section having a heart icon corresponding to heart-related information of the biometric information, an activity icon corresponding to activity-related information of the biometric information, and a battery icon corresponding to battery-related information of the implanted heart device.

5. The system of claim 1, wherein
displaying the second alert comprises displaying:
the therapy data indicating that the shock was delivered by the implanted heart device;
the second icon of the second video;
a cause that triggered the shock to be delivered by the implanted heart device; and
a time of the second alert; and
the second classification.

6. The system of claim 1, wherein
the first classification comprises diagnostic alerts; and
the second classification comprises therapy alerts.

7. The system of claim 1, wherein the list of alerts comprises a third alert of a third classification, wherein the first alert, the second alert, and the second alert are arranged vertically on the user interface, the third classification comprises hardware alert indicating hardware status of the implanted heart device.

8. The system of claim 1, wherein the one or more processors to:
determine an action of the patient on the user interface when the second video is displayed on the user interface; and
in response to determining the action, causes the first video to be displayed.

9. The system of claim 1, wherein
the first alert is overlayed on at least a portion of the first video when the first video is being displayed in the user interface; and
the second alert is overlayed on at least a portion of the second video when the second video is being displayed in the user interface.

10. The system of claim 1, wherein the first icon is located at an end of the first alert, and the second icon is located at an end of the second alert.

11. A method for accessing and displaying data related to an implanted heart device of a patient, the method comprising:
receiving, by a wireless transceiver of a mobile device, raw data in real time from an implanted heart device;
generating by the mobile device based on the raw data, biometric data indicative of at least one of heart beats per minute (BPM), pacing data, ventricular tachycardia, or atrial fibrillation;
obtaining, by the mobile device in response to a shock delivered by the implanted heart device to a patient, therapy data indicating that the shock was delivered by the implanted heart device;
generating, by the mobile device based on the biometric data, readable data summarized in a language that is understandable to the patient;
displaying, by the mobile device, a first alert of a first classification at a first portion of a user interface of the mobile device, the first alert including the readable data and the biometric data; and
displaying, by the mobile device, second alert of a second classification at a second portion of the user interface, the second alert including the therapy data in response to the shock delivered by the implanted heart device to the patient and in real-time, wherein the user interface displays a list of alerts of a plurality of classifications arranged vertically on the user interface, the list of alerts comprising the first alert and the second alert, wherein the first alert comprises a first icon of a first video, and the second alert comprises a second icon of a second video;
determine that the patient selects the first icon or the second icon, and
in response to determining that the patient selecting the first icon, display the first video about the biometric data with the first alert; and
in response to determining that the patient selecting the second icon, display the second video about the delivery of the shock by the implanted heart device with the second alert.

12. The method of claim 11, further comprising:
receiving, by the mobile device, activity data from an activity-tracking device; and
displaying, by the mobile device, activity-related information based on the activity data.

13. The method of claim 11, further comprising:
displaying, by the mobile device, battery information of the implanted heart device based on the raw data received from the implanted heart device.

14. A non-transitory computer readable medium including one or more instructions stored thereon and executable by a processor to:
receive raw data from an implanted heart device of a patient in real time;
generate, based on the raw data, biometric data indicative of at least one of heart beats per minute (BPM), pacing data, ventricular tachycardia, or atrial fibrillation;
obtain, by the mobile device in response to a shock delivered by the implanted heart device to a patient, therapy data indicating that the shock was delivered;
generate, based on the biometric data, readable data summarized in a language that is understandable to the patient;

display a first alert of a first classification at a first portion of a user interface of the mobile device, the first alert including the readable data and the biometric data on a user interface of a display; and display second alert of a second classification at a second portion of the user interface, the second alert including one or more the therapy data on the display in response to the shock delivered by the implanted heart device to the patient and in real-time, wherein the user interface displays a list of alerts of a plurality of classifications arranged vertically on the user interface, the list of alerts comprising the first alert and the second alert, wherein the first alert comprises a first icon of a first video, and the second alert comprises a second icon of a second video;

determine that the patient selects the first icon or the second icon, and in response to determining that the patient selecting the first icon, display the first video about the biometric data with the first alert; and in response to determining that the patient selecting the second icon, display the second video about the delivery of the shock by the implanted heart device with the second alert.

15. The non-transitory computer readable medium of claim 14, further comprising one or more instructions executable by the processor to:
receive activity data from an activity-tracking device and display activity-related information based on the activity data on the display.

16. The non-transitory computer readable medium of claim 14, further comprising one or more instructions executable by the processor to:
display battery information of the implanted heart device on the display based on the raw data received from the implanted heart device.

17. The non-transitory computer readable medium of claim 14, further comprising one or more instructions executable by the processor to:
generate one or more graphs based on the raw data received from the implanted heart device; and
display the one or more graphs on the display.

18. The non-transitory computer readable medium of claim 17, wherein the one or more graphs include
a graph of heart beats per minute received from the implanted heart device over a first predetermined time period,
a graph of activity over a second predetermined time period, or
a graph of ventricular pacing and atrial pacing over a third predetermined time period.

19. The non-transitory computer readable medium of claim 14, further comprising one or more instructions executable by the processor to:
display a user interface including a dashboard section having a having a heart icon corresponding to heart-related information, an activity icon corresponding to activity-related information, and a battery icon corresponding to battery-related information of the implanted heart device on the display.

* * * * *